US00PP32453P2

(12) United States Plant Patent
Holtmaat

(10) Patent No.: US PP32,453 P2
(45) Date of Patent: Nov. 10, 2020

(54) ***RUDBECKIA* PLANT NAMED 'RUDFA538'**

(50) Latin Name: *Rudbeckia hirta*
Varietal Denomination: RUDFA538

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,155

(22) Filed: Feb. 15, 2020

(30) Foreign Application Priority Data

Jan. 6, 2020 (QZ) ..... PBR 2020/0016

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./263.1, 474
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Rudbeckia* plant named 'RUDFA538' that is characterized by its vigorous growth habit, yet compact plant habit, its inflorescences with an average of 4 whorls of ray florets, its very floriferous blooming habit, and its inflorescences with ray florets that are grey-yellow to yellow when opening and changes to grey-purple to grey-orange when fully open.

2 Drawing Sheets

Botanical classification: *Rudbeckia hirta.*
Variety denomination: 'RUDFA538'.

CROSS REFERENCE TO A RELATED APPLICATION

This application claims priority to European Community Plant Variety Office (CPVO) Plant Breeder's Rights Application No. 2020/0016 filed on Jan. 6, 2020 under 35 U.S.C. 119(f), the entire contents of which is incorporated by reference herein.

BACKGROUND OF THE INVENTION

The present invention relates to a new and distinct cultivar of *Rudbeckia hirta* and will hereafter by referred to by its cultivar name, 'RUDFA538'. The new cultivar is an herbaceous perennial grown for use as a landscape plant.

'RUDFA538' was derived from a breeding program conducted by the Inventor at a nursery in Zuidwolde, The Netherlands. The objective of the breeding program was to select new cultivars of *Rudbeckia* with floriferous blooming habits and compact plant habits.

'RUDFA538' was selected in July of 2018 by the Inventor from amongst seedlings in a trial field that had been planted with seed derived from open pollination of numerous unpatented and unnamed proprietary plants from the Inventor's breeding program in July of 2017. The exact parentage is therefore unknown.

Asexual propagation of the new cultivar was first accomplished under the direction of the Inventor by tissue culture using meristematic tissue in Heerhugowaard, The Netherlands in March of 2019. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures includes but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDFA538' as a unique cultivar of *Rudbeckia.*

1. 'RUDFA538' exhibits a vigorous growth habit, yet compact plant habit.
2. 'RUDFA538' exhibits inflorescences with an average of 4 whorls of ray florets.
3. 'RUDFA538' exhibits a very floriferous blooming habit.
4. 'RUDFA538' exhibits inflorescences with ray florets that are grey-yellow to yellow when opening and changes to grey-purple to grey-orange when fully open.

'RUDFA538' can be compared to the *Rudbeckia* cultivars 'Sahara' (not patented), and 'Maya' (not patented). 'Sahara' and 'Maya' are both similar to 'RUDFA538' in plant height and in having multiple rows of ray florets. 'Sahara' differs from 'RUDFA538' in having ray florets that are coppery orange in color throughout the entire flowering season. 'Maya' differs from 'RUDFA538' in having ray florets that are deep yellow in color throughout the entire flowering season.

BRIEF DESCRIPTION OF THE DRAWINGS

The accompanying colored photographs illustrate the overall appearance and distinct characteristics of the new *Rudbeckia*. The photographs were taken of a 5.5-month-old plant of 'RUDFA538' as grown outdoors in a 17-cm container in Zuidwolde, The Netherlands.

The photograph in FIG. 1 is a side view of 'RUDFA538' in bloom.

Figure 1:
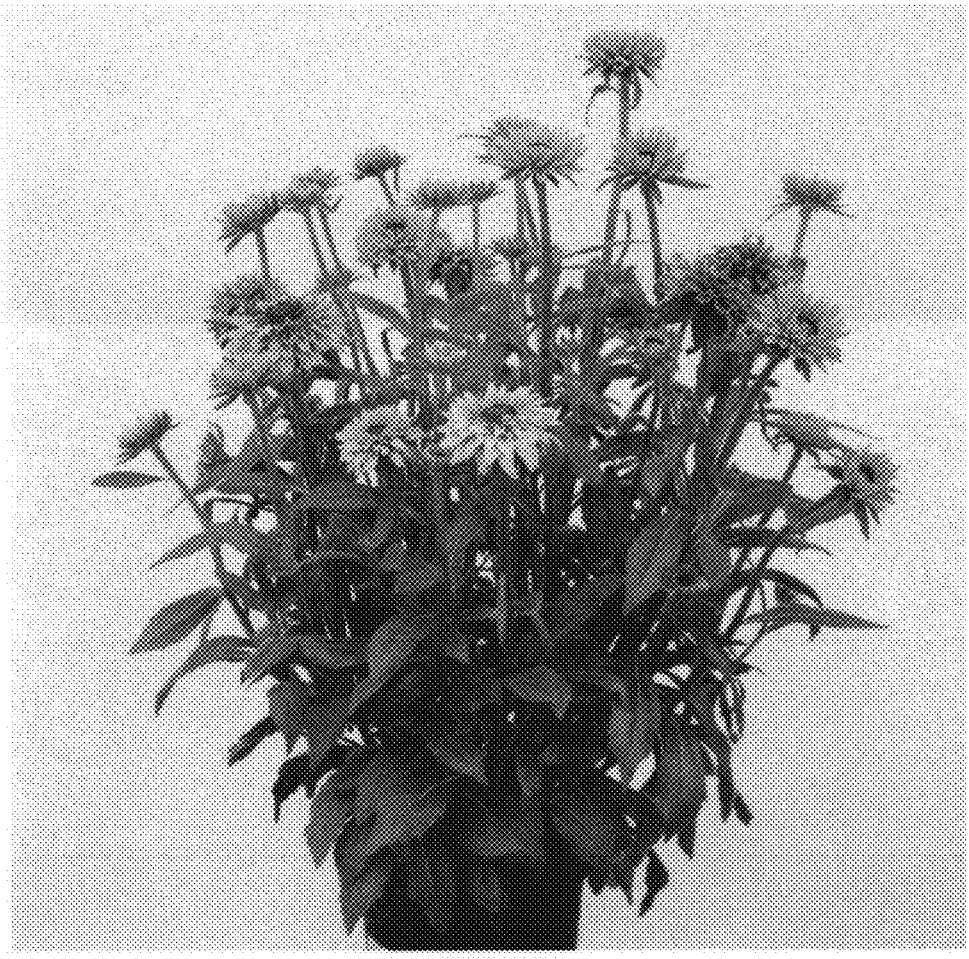
Figure 2:
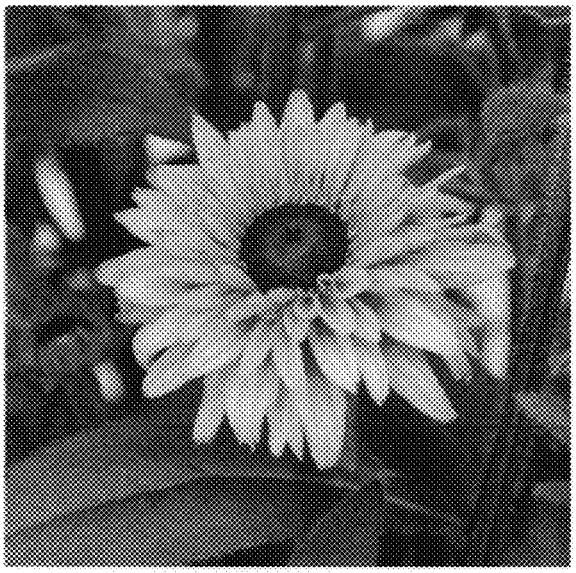

The photograph in FIG. 2 provides a close-up view of the young inflorescences of 'RUDFA538'.

Figure 3:
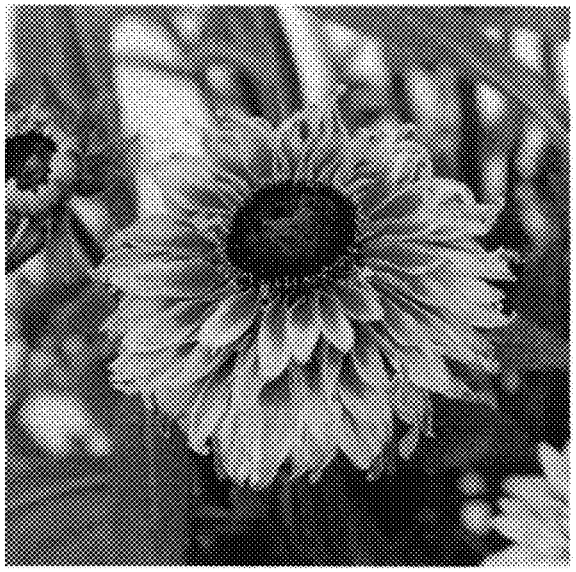

The photograph in FIG. 3 provides a close-up view of the mature inflorescences of 'RUDFA538'.

Figure 4:
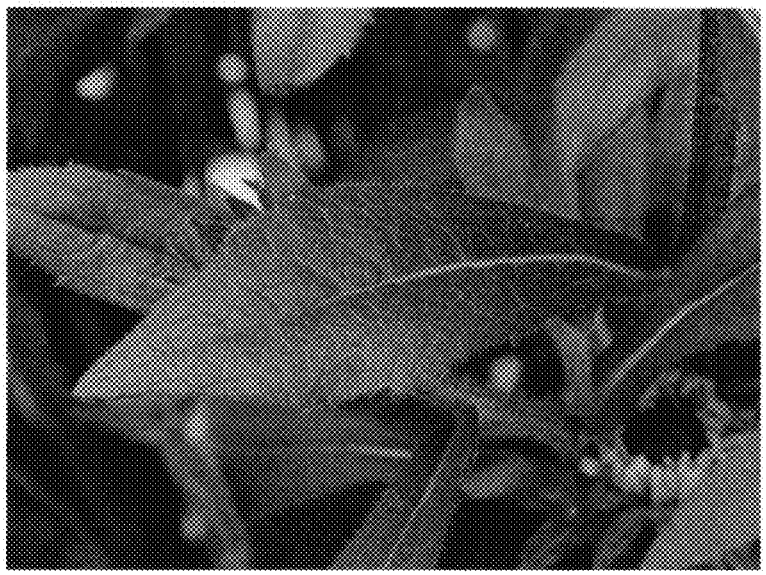

The photograph in FIG. 4 provides a close-up view of the foliage of 'RUDFA538'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 5.5-month-old plants of 'RUDFA538' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in The Netherlands.

*Plant type*.—Perennial.

*Plant habit*.—Upright, compact.

*Plain shape*.—Narrow obovate.

*Height and spread*.—Average of 56 cm in height from soil level to top of foliar plane and 60 cm in height from soil level to top of floral plane, 50.8 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous, yet compact.

Stem description:

*Shape*.—Moderately angled.

*Stem color*.—Young stems; 146C, N77A to N77B at the angles. mature stems; 143B, N186C at the angles.

*Stem size*.—An average of 5.5 mm in diameter and an average of 29.4 cm in height.

*Stem surface*.—Moderately glossy and densely covered with strigose hairs an average of 2 mm in length and close to 155A in color.

*Stem number*.—Average of 11 main stems, 4 lateral branches per main stem.

*Internode length*.—An average of 3.2 cm in length.

*Stem aspect*.—Main stems; average of 15° to vertical, lateral branches; average of 20° to main stems.

*Branching*.—Freely branching from base with lateral stems.

Foliage description:

*Leaf shape*.—Broadly ovate.

*Leaf division*.—Simple.

*Leaf base*.—Cuneate.

*Leaf apex*.—Acute.

*Leaf venation*.—Pinnate, color upper surface 145A, color lower surface 146C.

*Leaf margins*.—Coarsely serrate, coarsely and very slightly undulate.

*Leaf attachment*.—Petiolate.

*Leaf arrangement*.—Alternate.

*Leaf size*.—Average of 10.6 cm in length and 3.9 cm in width.

*Leaf color*.—Young upper surface; 137B, young lower surface; 138A, mature upper surface: NN137A, mature lower surface; 147B.

*Leaf surface*.—Upper surface matte, and non-rugose, rough to touch, lower surface is matte, slightly rugose, rough to touch, both surfaces densely pubescent with short strigose hairs; an average of 1.5 mm in length and N155D in color.

*Petioles*.—Average of 1.9 cm in length, flattened, average diameter at widest point 1.1 cm and at narrowest point 4 mm, upper surface color; 145A with margins NN137B, lower surface color; 146A to 146B with margins 147B, both surfaces slightly glossy and densely covered with strigose hairs; an average of 1.5 mm in length and N155D in color.

Flower description:

*Type*.—Terminal capitulum, consisting of ray florets and disk florets.

*Capitulum number*.—5 per stem, up to 75 per plant.

*Lastingness of inflorescence*.—Average of 2 weeks, persistent.

*Capitulum size*.—Matures to about 6.3 cm in height and 9.3 cm in diameter, disk size is an average of 2.8 cm in diameter.

*Fragrance*.—None.

*Involucral bracts* (*phyllaries*).—Cuneate base, acute apex, narrow ovate to narrow elliptic in shape, entire margins, average of 42 arranged in two rows, 3.3 cm in length and 9 mm in width, color; upper surface when fully open NN137A, lower surface when fully open 138A, both surfaces and margins matte and densely covered with strigose hairs; an average of 1.5 mm in length and NN155D in color.

*Receptacle*.—Near orbicular in shape, an average of 1 cm in height and diameter, 157D in color.

*Buds*.—Globular in shape, immature ray florets pointed upward and curling inward, up to 2 cm in length and 5.1 cm in diameter, immature ray florets are 151D in color, immature involucral bracts upper surface NN137A, lower surface 138A, surface on involucral bracts and immature ray florets is densely covered with strigose hairs; an average of 1.5 mm in length and NN155D in color.

*Peduncle*.—Strong, straight on top of main flowering stem, average of 7.2 cm in length and 6 mm in diameter, color: 145B and axially striped 143B, surface moderately glossy sand densely covered with short strigose hairs; an average of 2 mm in length and NN155D in color.

*Ray florets*.—Average of 100, rotate around the disk, oblong in shape, average of 4.2 cm in length and 1.3 cm in width, emarginate apex, cuneate base, entire margin, both surfaces are velvety, matte and glabrous, held near horizontal, color; when opening upper surface; lower ⅓$^{rd}$ 185A, upper ⅔$^{rd}$ 11A, when opening lower surface; lower ⅔$^{rd}$ 160A to 160B, upper ⅓$^{rd}$ 1B, when fully open upper surface and veins; lower ⅔$^{rd}$ 187B, upper ⅓$^{rd}$ 174D, when fully open lower surface; 177C, flushed with 184D, veins N144A.

*Disk flowers*.—Average of 800, tubular, 20 whorls arranged spirally on a conical receptacle, lower 90% fused into tube, upper 10% free, about 8 mm in length and 3 mm in width, free lobes have entire margins and are curled backwards, both surfaces glabrous and moderately glossy, color; when opening and fully open upper and lower surface 200A and 203A, changing to 159C at the base, spines; none, bracts. — 1 per disk floret, spirally placed on disk, soft, flattened, an average of 7 mm in length and 1 mm in diameter, oblanceolate in shape, acute apex, narrow cuneate base, color apex; N186C, color mid-section and base; NN155B, color margins; N186C.

Reproductive organs:

*Gynoecium*.—Pistil; 1, 7 mm in length, style; 5 mm in length, color; 200A, mid-section and base 158D, stigma; cleft, decurrent, 3 mm in diameter, 203A in color, ovary; 155C in color.

*Androecium*.—Stamens; 5, filaments; 2.5 mm in length, 158D in color, anther; narrow oblong in shape, 2.5 mm in length, 0.5 mm in width, 200A and 203A in color, pollen; moderate in quantity and 17B in color.

*Fruit/seed*.—None observed to date.

It is claimed:

1. A new and distinct cultivar of *Rudbeckia* plant named 'RUDFA538' substantially as herein illustrated and described.

* * * * *